United States Patent [19]

Steinberg

[11] Patent Number: 4,769,032
[45] Date of Patent: Sep. 6, 1988

[54] PROSTHETIC VALVE AND MONITORING SYSTEM AND METHOD

[76] Inventor: Bruce Steinberg, 9817 Layton Rd., Philadelphia, Pa. 19115

[21] Appl. No.: 836,496

[22] Filed: Mar. 5, 1986

[51] Int. Cl.⁴ .............................................. A61F 2/24
[52] U.S. Cl. ...................................... 623/2; 623/900; 128/668
[58] Field of Search ...................... 623/2, 900; 128/1.3, 128/1.5, 653, 668, 691, 692

[56] References Cited

U.S. PATENT DOCUMENTS

| | | | |
|---|---|---|---|
| 3,197,788 | 8/1965 | Segger | 623/2 |
| 3,487,826 | 1/1970 | Barefoot | 128/692 |
| 3,516,399 | 6/1970 | Barefoot | 128/692 |
| 3,529,591 | 9/1970 | Schuette | 128/692 |
| 3,696,674 | 10/1972 | Spencer | 623/2 X |
| 3,959,827 | 6/1976 | Kaster | 623/2 |
| 4,038,703 | 8/1977 | Bokros | 623/2 |
| 4,245,358 | 1/1981 | Moasser | 623/2 |
| 4,349,498 | 9/1982 | Ellis et al. | 623/2 X |

*Primary Examiner*—Ronald L. Frinks
*Attorney, Agent, or Firm*—Christie, Parker & Hale

[57] ABSTRACT

A prosthetic heart valve which can be externally monitored is disclosed. In a first embodiment, the leaflets of the valve are magnetized, and the voltage induced in a coil juxtaposed thereto may be monitored. In a second embodiment, conductors are integrated with the leaflets. When the valve is then placed in a magnetic field, a voltage is induced in the conductors. The voltages induced in both valve configurations may be analyzed to indicate valve operation and conditions.

87 Claims, 6 Drawing Sheets

Fig. 1

PROSTHETIC VALVE AND MONITORING SYSTEM AND METHOD

BACKGROUND OF THE INVENTION

Field of the Invention

This invention relates generally to an improved prosthetic heart valve and to an instrument and method for measuring the velocity of heart leaflets moving in a heart valve, in order to monitor valve condition and performance. More particularly, the instrument measures quantitatively a voltage induced by the motion of the heart leaflet in the heart valve.

For several years, both porcine and nonporcine artificial heart valves have been used for replacement of degenerating heart valves. Monitoring the condition of these prosthetic valves is important. Particularly in the case of porcine artificial heart valves, "early calcification and tearing is a life threatening complication that must be recognized promptly and treated by emergency valve replacement." B. F. Lewis, *Early Calcification and Obstruction of a Microporcine Bioprosthesis*, Annals of Thoracic Surgery, 30(6): 592-4 (Dec. 1980). Several studies indicate that a very large percentage of the recipients of porcine artificial heart valves are susceptible to heart failure due to the tearing and/or calcification of the valve leaflets. J. L. Bosch, *Late Tears in Leaflets of Porcine Bioprosthesis in Adults*, Annals of Thoracic Surgery, 37(1):78-93 (Jan. 1984). In addition, both porcine and nonporcine artificial heart valves are subject to malfunctions in operation due to degeneration, thrombosis, endocarditis, bacterial infection, etc.

In general, malfunctions of artificial heart valves occur suddenly and without warning. Therefore, recipients of artificial heart valves are subject to a continual possibility of unexpected valve malfunction and deleterious heart failure. To some extent the possibility of malfunction can be evaluated by periodic testing. At present, the most common method of evaluating artificial heart valve operation is by way of an echocardiogram. This test is very expensive and requires a time delay prior to diagnosis of the echocardiogram test results. In addition, this test can only be performed at established health facilities which have suitable echocardiogram equipment and staff personnel trained and qualified for performing the test and interpreting the test results.

Therefore, it is the object of the present invention to provide an improved method of monitoring the operation of an artificial heart valve, which in particular will enable monitoring of subtle changes in the leaflet structure of the valve in an inexpensive, non-invasive, substantially real-time manner, on a continual or periodic basis.

SUMMARY OF THE INVENTION

The present invention replaces the need for an echocardiogram by allowing the recipient to monitor his own valve continuously at home, or periodically in a doctor's office or in a medical clinic, or other health care facility, etc.

According to the invention, an artificial heart valve is provided with means for generating a detectable electrical current upon motion of the valve leaflets responsive to blood flow therethrough. The current signal can then be analyzed to determine the leaflet's condition.

Generally, the apparatus of the invention operates on the principle of electromagnetic induction. Specifically, the invention operates according to Faraday's Law:

$$V = \oint \vec{E} \cdot \vec{dl} = - \frac{d\Phi}{dt}$$

and the electromotive force law for static magnetic fields:

$$V = \int (\vec{U} \times \vec{B}) \cdot dl$$

For a more detailed description of the principles of electromagnetic induction, reference is made to Cheng, *Field and Wave Electromagnetics*, Addison-Wesley Publishing Company, 272-283 (1983).

In the preferred embodiment of the invention, the leaflets of an artificial heart valve are impregnated with magnetizing ions prior to implantation of the valve into the heart. Thereafter, blood flow through the heart valve opens the ion-impregnated heart leaflets. The motion of the leaflets induces a voltage in a solenoid coil juxtaposed to the valve. The voltage varies in accordance with the velocity at which the valve leaflets open, following Faraday's Law for time varying magnetic fields:

$$V = \oint \vec{E} \cdot \vec{dl} = - \int \frac{d}{dt}\vec{B}(t) \cdot ds = - \frac{d\Phi}{dt}$$

In these equations,

V=electromotive force induced;
$\vec{E}$=induced electric field;
$\Phi$=magnetic flux;
$d\vec{B}/dt$=Time-varying magnetic field generated by the movement of the magnetized leaflet; and ds=surface encircled by the solenoid coil.

The signal voltage induced in the solenoid coil can then be detected by a sensitive potentiometer and amplified for analysis. For example, diagnostic analysis can be performed by a microprocessor-controlled system or presented on an oscilloscope for analysis by a physician.

In a second embodiment of the invention, the leaflets of the artificial heart valve are impregnated with conductors, which may be actual wires or may be formed by ion-impregnation in the shape of a conductive coil prior to implantation of the valve into the heart. Thereafter, motion of blood flow through the heart valve opens the conductor-impregnated leaflets. If a constant magnetic field is juxtaposed to the valve, the motion of the leaflets induces a voltage in the conductors. The voltage varies in accordance with the velocity with which the valve leaflets open. In this embodiment of the invention, the following electromotive force law equation, for static magnetic fields provides the measure of the induced voltage:

$$V = \int (\vec{U} \times \vec{B}) \cdot dl; \vec{U} = \frac{d\vec{y}}{dt}$$

In this equation:

V=electromotive force induced;
$\vec{B}$=uniform applied magnetic field;
L=length of the conductor; and
$d\vec{y}/dt$=velocity of the moving valve leaflet.

In the case when the conductor is a loop, the voltage induced therein will follow Faraday's Law:

$$V = \frac{d\vec{B}}{dt} \circ \int ds = -\frac{d\Phi}{dt} = \frac{-d}{dt} \int \vec{B(t)} d\vec{s}$$

In these equations,
V=electromotive force induced;
$\vec{B}$=uniform applied magnetic field;
ds/dt=rate at which the surface of the valve moves in relation to the magnetic field; and
Φ=flux of the magnetic field.

Faraday's Law also applied when the conductor is impregnated over an area on the surface of the leaflets.

The signal voltage induced in the conductors can then be detected by a sensitive potentiometer and amplified for analysis, as above.

BRIEF DESCRIPTION OF THE DRAWINGS

The invention will be better understood if reference is made to the accompanying drawings, in which:

FIG. 1a' is a coil-integrated leaflet (CIL) porcine mitral heart valve prosthesis, shown in atrial view, having had its leaflets impregnated with conductors.

FIGS. 1b' is a CIL porcine mitral heart valve prosthesis shown in ventricular view, with its leaflets impregnated with conductors.

FIG. 1c' is a CIL porcine mitral heart valve prosthesis shown in side view, with its leaflets impregnated with conductors.

FIG. 2a shows the preferred incision;
FIG. 2b shows the cannulae introduced into the heart;
FIG. 2c shows the mitral valve;
FIG. 2d shows the mitral valve and papillary muscles excised;
FIG. 2e shows the prosthetic valve inserted;
FIG. 2f shows a catheter placed across the valve; and
FIG. 2g shows the incision to the heart being closed.

FIG. 3a shows the preferred incision;
FIG. 3b shows the aortic valve exposed after incision;
FIG. 3c shows the porcine valve;
FIG. 3d shows the porcine valve sutured into place;
FIG. 3e shows the porcine valve positioned within the aorta; and
FIG. 3f shows the incision closed.

DETAILED DESCRIPTION OF THE PREFERRED EMBODIMENTS

In the past, electromagnetic induction principles have been used in the application of blood flow probes. The probes quantitatively measure the volumetric rate of blood flow through blood vessels. See U.S. Pat. Nos. 3,487,826, 3,696,674, 3,529,591, and 3,516,399. The operation of the devices described in these patents is based upon the induction of a voltage through a conductor (blood) moving through a uniform applied magnetic field. The magnitude of the induced voltage, in such cases, is determined by the velocity of the blood, the strength of the field, and the length of the conductor. This device can be modeled by the electromotive force law for static magnetic fields as described in the following equation.

$$V = \int (\vec{U} \times \vec{B}) \cdot dl; \vec{U} = \frac{d\vec{y}}{dt}$$

where V is the electromotive force induced,
$\vec{B}$ is the uniform magnetic field,
L is the length of the conductor, that is, the width of the blood vessel, and
dy/dt is equal to the velocity of the moving conductor, that is, to the blood flow rate.

As mentioned, the conductor in these systems is actually the blood flowing past reference points defined by the positions of the probe electrodes. In order to sense the flow, these electrodes must make direct contact either with the blood or the outer surface of the vessel wall.

The prosthetic valve of the invention, in both magnetized leaflet and coil-integrated leaflet forms, operates on entirely different principles than do the electromagnetic blood flow meters described in the patents listed above. In the prior art blood flow meters, the magnetic field is uniform and the flowing blood is the conductor in which an electromotive force is induced. In the magnetized leaflet embodiment of the present invention, the motion of the leaflet produces a varying magnetic field. A voltage is then induced in the juxtaposed coil of wire, in contrast to the blood flow meters discussed above, which use an applied field to induce a voltage in the blood. No current or voltage need be supplied to the artificial valve of the invention for signal generation. In the coil-integrated embodiment of the invention, motion of the conductor integrated within the leaflet in an applied uniform magnetic field induces a voltage therein which can be directly measured.

More specifically, the measurement technique of the invention permits a direct indication of the motion of the leaflet, which is a direct indication of its condition. By comparison, the blood flow meters discussed above measure only the velocity of the blood. This is a very important clinical distinction. Observing the motion of the leaflets is a much more accurate indicator of the condition of the leaflets. Observing only the velocity of the blood through the valve will not provide an indication of degradation of the leaflets in all cases. For example, blood flow meters may not allow detection of a calcified, stenotic heart valve. The leaflets of a stenotic heart valve do not move, although blood may still flow through the valve at its normal rate. By comparison, the method of the invention provides a direct indication of the movement of the leaflets. Thus, stationary leaflets will be detectable using the system of the invention.

Figure 1:
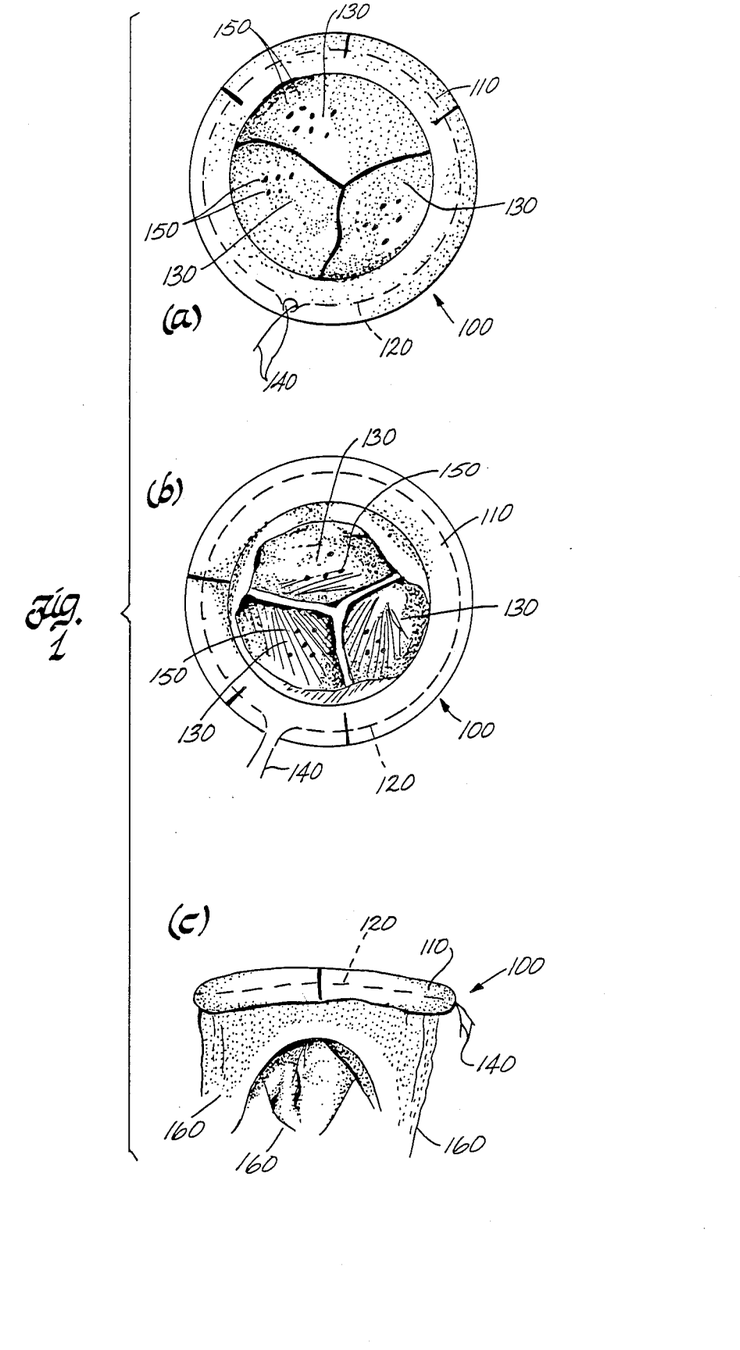
FIG. 1a is a magnetized-leaflet (MIL) porcine mitral heart valve prosthesis, shown in atrial view, having had its leaflets impregnated with magnetizing ions and showing the signal wires wrapped concentrically around the base of the MIL porcine heart valve.
FIG. 1b is a MIL porcine mitral heart valve prosthesis shown in ventricular view, with its leaflets impregnated with magnetizing ions and showing signal wires wrapped concentrically around the base of the MIL porcine heart valve.
FIG. 1c is a MIL porcine mitral heart valve prosthesis shown in side view, with its leaflets impregnated with magnetizing ions and showing signal wires wrapped concentrically around the base of the MIL porcine heart valve.

In FIG. 1, an MIL valve prosthesis is shown having been equipped with a solenoid coil. Typically such prostheses are manufactured together with supporting structure (such as the woven material shown in FIG. 1) of plastic, metal or combination thereof. According to the invention, a solenoid coil of concentrically wrapped wires 120 is tightly packed within the base 110 of the valve 100. The solenoid coil 120 is encased by a nontoxic substance which is accepted by the surrounding tissue. Two leads 140 connect the coil to the analysis equipment (not shown). In this embodiment of the invention, each of the heart leaflets 130 is implanted with magnetizing ions or is surgically impregnated with magnetizing iron oxide covered by a non-toxic substance which is acceptable to the surrounding tissue. Motion of the magnetized prosthetic leaflets then induces a current in the coil 120. The current can be monitored for analysis of valve condition and performance.

FIG. 1a provides an atrial view of the MIL valve, which the ventricular view is provided in FIG. 1b. In this case the valve is porcine, but other types of prosthetic valves are within the scope of the invention. In both figures it will be noted that the solenoid coil 120 is concentrically wrapped about the base 110 of the heart valve 100, and that the heart leaflets 130 are indicated as having been implanted or impregnated with magnetizing ions at 150. FIG. 1c shows a side view of the MIL valve, and indicates the location of the solenoid coil 120 within the base 110 of MIL valve 100. Stationary leaflet supports 160 extend vertically downward from the base 110 of the porcine heart valve 100 and contact the leaflets 130 as they open.

Prior to insertion of a MIL mitral valve prosthesis into a heart, the necessary elements of the MIL valve must be incorporated, and the valve leaflets must be magnetized. In the case of a porcine valve, the solenoid coil is incorporated into the base 110 of the artificial heart valve. The solenoid coil is treated with a nontoxic substance so that the surrounding body tissue does not reject it.

In FIG. 1', a CIL valve prosthesis is shown equipped with conductors. Again the prosthetic valve can be porcine or otherwise, and is manufactured together with supporting structure (such as the woven material shown in FIG. 1') of plastic, metal or both. According to the invention, conductors 165, 170 and 180 are impregnated in the leaflets 130 of the porcine valve 100. The conductors 165, 170 and 180 are encased by a non-toxic substance which is accepted by the surrounding tissue. Two leads 190 are connected to each conductor 165, 170 and 180 and to the analysis equipment (not shown). The conductors may be formed by ion implantation in a suitable circuit pattern or by surgical impregnation with actual wire conductors.

FIG. 1a' provides an atrial view of the CIL valve, while the ventricular view is provided in FIG. 1b'. In both figures it will be noted that the conductors 165, 170 and 180 are implanted or impregnated into the leaflets. FIG. 1c' shows a side view of the CIL valve, including leads 190 extending from conductors 165, 170 and 180. Leaflet supports 160 extend vertically downward from the base 110 of the porcine heart valve 100 and contact the leaflets 130 as they open.

Prior to insertion of a CIL porcine or non-porcine mitral valve prosthesis into a heart, the valve leaflets are impregnated with the conductors 160, 170 and 180. The conductors are treated with a nontoxic substance so that the surrounding body tissue does not reject it. Thereafter, if the patient is placed in a magnetic field, a current will be induced in the coil upon motion of the leaflets. The current can be detected for analysis of valve performance.

The magnetization of the leaflets of the MIL valve of the invention may be accomplished by surgical implantation of magnetic material, for example, iron oxide or samarium cobalt pellets. The coil of the CIL embodiment of the invention may be similarly surgically implanted. Either embodiment of the invention may be implemented by following the procedure set forth generally in Picraux and Pearcy, *Ion Implanation of Surfaces,* Scientific American, (March 1985) pp. 102–112, which is incorporated by reference herein. According to that technique, a beam of magnetizing ions is electrostatically accelerated into the surface of a material. In this way, a controllable quantity of almost any element can be mingled with a host material. In this case an artificial heart valve leaflet, made either of porcine or non-porcine subtances, can be implanted with foreign ions, either magnetizing or conductive ions, to form a thin layer of substantially any desired configuration at any predetermined depth.

More specifically, ions of the material to be implanted originate at one end of an accelerator in a chamber in which electrons boil from a heated filament. The ions are accelerated by electric fields. Another electric field draws the ions from the chamber. The beam of ions is focused and accelerated to high energies, typically between 10 and 500 kiloelectron volts. Just before the ions strike the target, varying electric fields created by charged plates deflect the beam to eliminate neutral particles and to sweep the beam across the target for a uniform surface treatment. It is possible to anticipate, and therefore to control, not only the depth and distribution of the implanted atoms, but also the change in composition (i.e. magnetic and conductive composition) which they produce in the host material.

In this manner, magnetizing and/or conductive ions can be ion-implanted in any desired configuration of lines, defining circles or areas on the heart leaflets, whether porcine or non-porcine, to create a valve which can be conveniently monitored. In the MIL embodiment, the leaflets would simply have a portion of their surfaces implanted with magnetic material. In the CIL embodiments, a circuit of conductive material would be created.

After surgical insertion of the valves as described below, motion of the leaflets can be detected. The MIL valve involves induction of a current in a coil due to the motion of magnetized material juxtaposed thereto, and follows Faraday's Law:

$$V = \oint \vec{E} \cdot \vec{dl} = -\frac{d}{dt} \int \vec{B}(t) \cdot \vec{ds} = -\frac{d\Phi}{dt}$$

where
  $V$ = electromotive force (emf) induced;
  $\vec{E}$ = induced electric field;
  $d\vec{B}/dt$ = Time-varying magnetic field due to motion of the magnetized leaflets;

$\vec{ds}$ = d (surface enclosed by the coil); and Φ=flux.

In the CIL embodiment conductors embedded in the leaflets move in a steady magnetic field, and a current is induced therein, obeying the following:

$$V = \int (\vec{U} \times \vec{B}) \cdot dl; \vec{U} = \frac{d\vec{y}}{dt}$$

V=emf induced;
B=uniform magnetic field;
dy/dt=velocity of the leaflet; and
l=length of the conductor.

The remaining steps in the method of the invention involve the insertion of an artificial porcine or non-porcine valve for replacement of any malfunctioning heart valve (i.e., the pulmonary, tricuspid, mitral or aortic valves.) The replacement of the mitral and aortic valves is discussed below. The surgical procedure described in Schwartz, *Principles of Surgery* 4th ed., pp. 826-841 (1985), incorporated by reference herein, for removal and replacement of heart valves, is followed.

Figure 2:
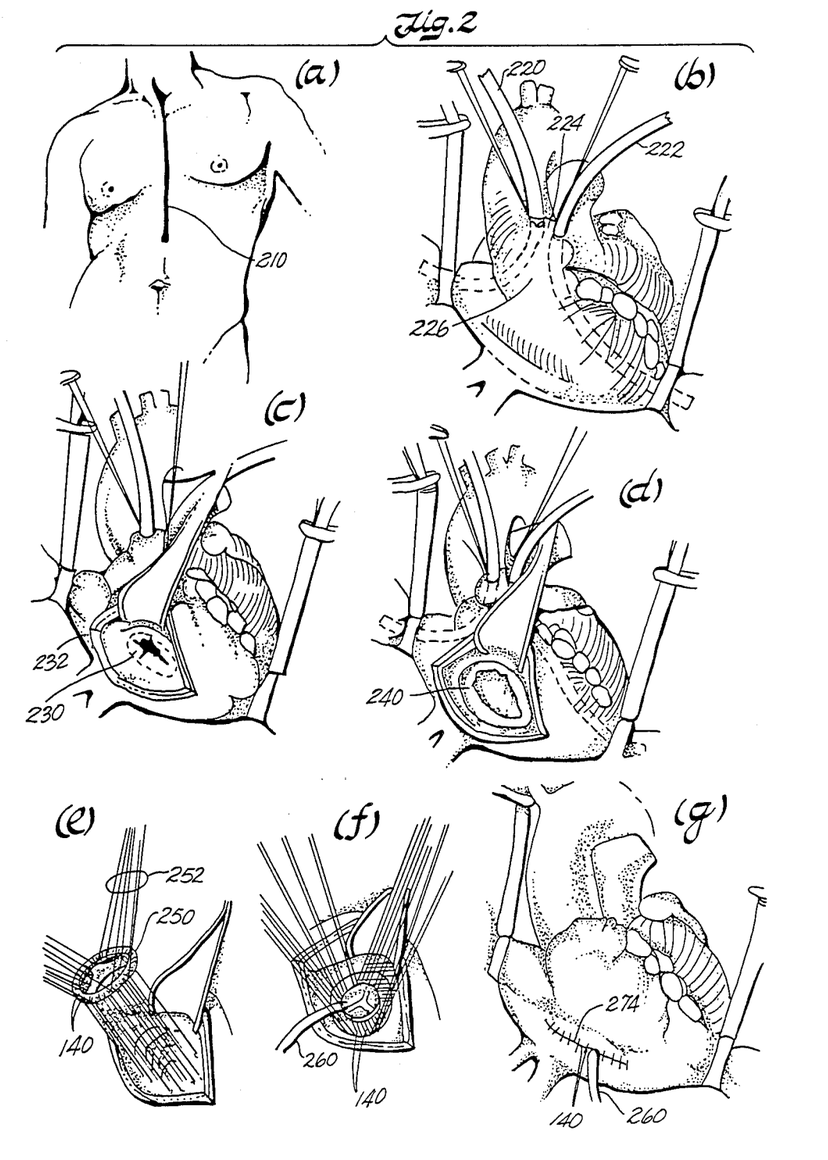
FIG. 2 shows the steps in the process of insertion of either a CIL or MIL porcine mitral heart valve prostheses into the heart, and includes the following sub-figures.

FIG. 2 depicts the sequence of steps for the replacement of the mitral valve following the method referred to in the *Principles of Surgery*. FIG. 2a shows the making of a median sternotomy incision 210 into the chest. As shown in FIG. 2b, cannulae 220 and 222 are introduced through the arterial wall 224 into the vena cava 226. These cannulae connect the patient to an external pump for performing the heart function during surgery. As shown in FIG. 2c, the mitral valve 230 is exposed with an incision in the left atrium 232 anterior to the point of entry of the right pulmonary veins. As shown in FIG. 2d, the mitral valve with the papillary muscles is completely excised leaving a small annulus 240. At this point, the cavity of the left ventricle is carefully inspected and a MIL or CIL, porcine or non-porcine mitral valve is selected. FIG. 2e shows insertion of the prosthesis 250, which is secured with 12-15 mattress sutures 252 of O-Dacron. These mattress sutures may be buttressed with Teflon pledgets on the ventricular surface. FIG. 2f shows a catheter 260 which is placed across the valve to keep the valve incompetent, that is, open, to avoid air embolism. Referring to FIG. 2g, the leads 140 connected to the coil in the MIL-valve and to the conductors in the CIL-valve are drawn through the atrial wall to the epicardium. Lastly, FIG. 2g shows the closing of the atriotomy incision 274 around the catheter 260, after which the heart is allowed to fill with blood and displace air. At that time, the catheter 260 is removed, which permits the left ventricle 272 to contract normally, and the heart function is resumed.

Figure 3:
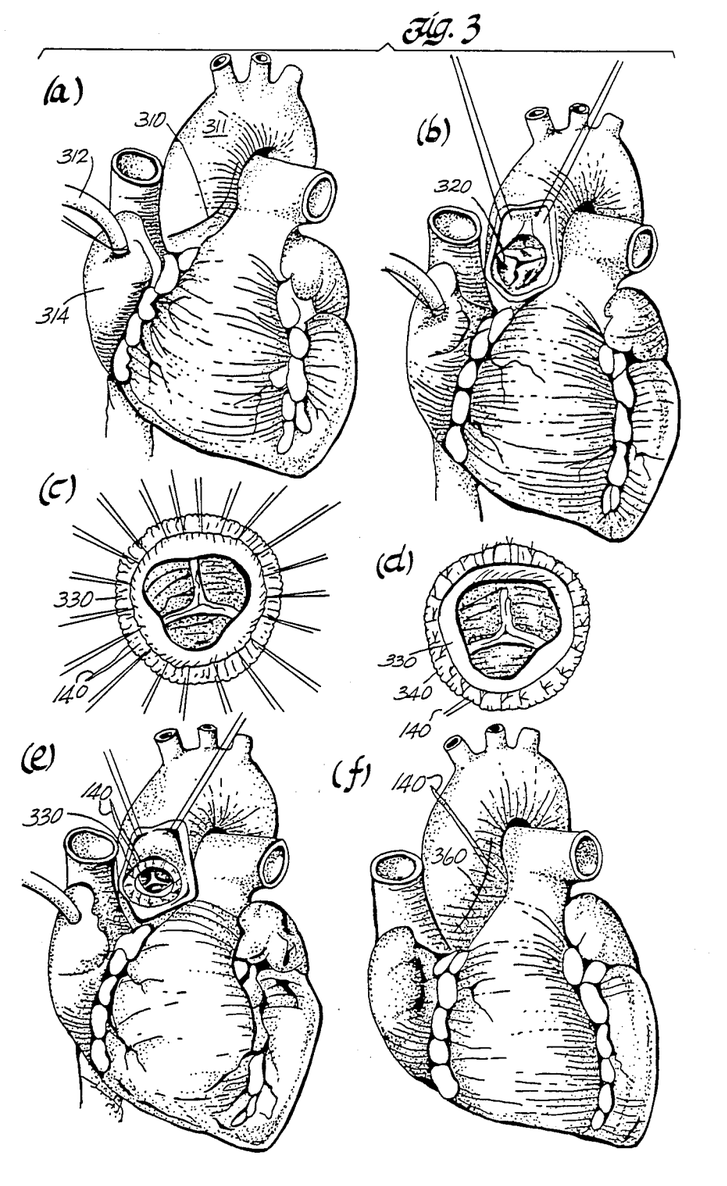
FIG. 3 shows the steps in the insertion of either a CIL or MIL aortic valve prosthesis into the heart, and includes the following subfigures.

The process of preparation and insertion of a MIL/CIL porcine/non-porcine aortic valve prosthesis into the heart is generally similar to that outlined above with respect to the mitral valve. The valve preparation steps, implanting the solenoid coil and magnetizing the artificial heart leaflets, of the MIL valve or forming coils on the leaflets of the CIL valve, are as described above. The replacement procedure described in Schwartz, *Principles of Surgery*, 4th ed., pp. 838-839 (1985), incorporated by reference herein, is preferred. As shown in FIG. 3a, a cardiopulmonary bypass is instituted following cannulation of the right atrium 314 with a single large cannula 312. The aorta is opened with an oblique incision 310, initially begun about a centimeter above the base of the right coronary artery 311. The aortic valve 320 is then excised as indicated at FIG. 3b. As shown in FIGS. 3c and 3d, the aortic valve prothesis 330 in either MIL or CIL configuration is sutured into position as shown at 340. In FIG. 3e, the valve 330 is sewn into the aortic cavity. The leads 140 connected to the coil of the MIL valve and to the conductors of the CIL valve are drawn through the aorta to the epicardium. Lastly, the aorta is closed with a synthetic suture 360 as shown in FIG. 3f.

After the MIL or CIL porcine or non-porcine valve has been secured into position, and the heart is operating, the operation of the valve can be monitored. As discussed above in connection with FIGS. 1 and 1', motion of the blood through the heart valve 100 opens the leaflets 130 of the valve. The motion of the heart leaflets 130 induces a voltage in the coil 120 of the MIL-valve, which may be monitored. If a patient having had a CIL-valve replacement installed as discussed above is then disposed in a magnetic field, a voltage is induced in the conductor formed on the leaflets. In either case, the voltage is proportional to the rate at which the leaflets on the MIL/CIL-valve open, as described by Faraday's Law, discussed above. If the leaflets on the MIL/CIL-valve are damaged, or become stiff, or if blood diffuses around the valve base 110, the leaflets do not open as rapidly, reducing the induced voltage. The voltage signal is thus directly indicative of valve function.

Figure 4:
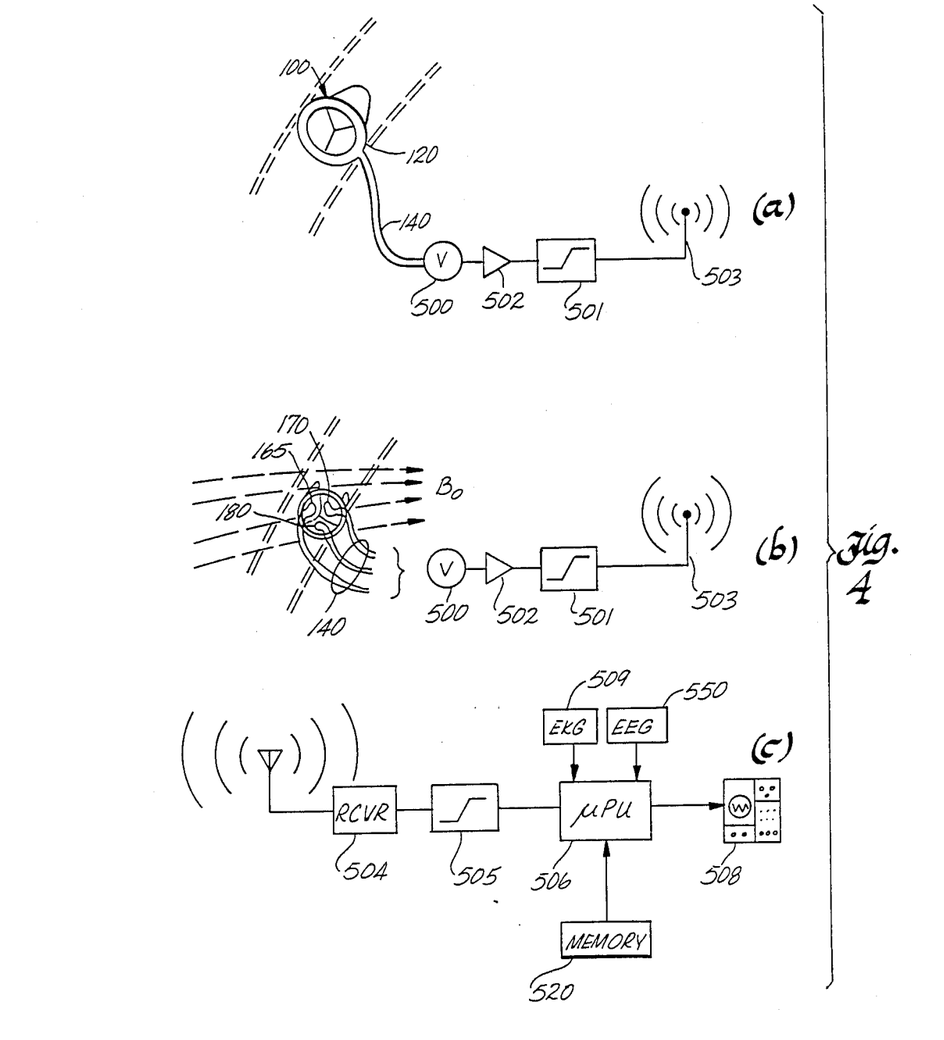
FIG. 4a shows a block diagram of the signal detection and conditioning electronics of the MIL system.
FIG. 4b shows a block diagram of the signal detection and conditioning electronics of the CIL valve monitoring system.
FIG. 4c shows the analysis system in block diagram form.

FIGS. 4a and 4b show both MIL and CIL embodiments in schematic form. In the MIL system (FIG. 4a), the coil 120, which is concentric with the prosthetic valve 100, is connected by leads 140 to a sensitive potentiometer 500 which is surgically implanted in the epicardium, in an adjacent body cavity or on the body surface. Similarly, in the CIL system (FIG. 4b), conductors 165, 170 and 180 which are implanted within the leaflets 130 of the prosthetic valve 100, are connected by leads 140 to a sensitive potentiometer 500 which is surgically implanted in either the epicardium, in an adjacent body cavity or on the body surface. The patient is exposed to a magnetic field $B_o$, which passes through the CIL-valve. The field can be generated either externally or internally to the patient's body. In the internal configuration, one or more solenoid coils are juxtaposed to the heart valve so that constant lines of magnetic flux are directed through the CIL-valve. In the external configuration, magnets direct lines of flux through the body cavity and through the CIL-valve.

Electronic signal detection, amplification, and processing apparatus is essentially similar in both embodiments of the invention. For example, potentiometer 500 detects the voltage signals generated from the valve. The potentiometer 500 is connected to a microamplifier 502, a filter 501 and suitable transmitter circuitry 503. The voltage signals induced by either the MIL or CIL valve are filtered at 501 for removal of noise generated by pacemakers, transistor radios, etc. The signal can then be provided to an analysis system (FIG. 4c). The connection can be by wire, or by wireless transmission as shown. The signal is transmitted at 503 to a receiver 504 external to the body. The voltage signals are then filtered a second time at 505 and are then supplied to a microprocessor controlled diagnostic system 506 for analysis. The voltage signals can be made available for presentation on an external oscilloscope 508 for analysis by a physician, or can be analyzed by microprocessor 506 for indication of dangerous valve conditions. Such analysis can include comparison to prior signals stored at 520, and correlation to data from other instruments as indicated at 509, 550.

Figure 5:
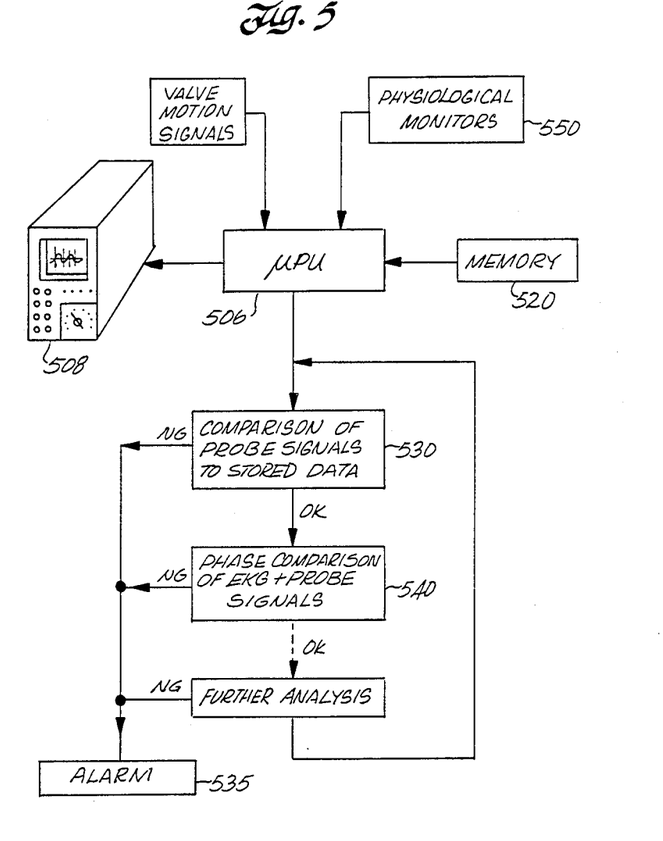
FIG. 5 shows a flowchart of the processing steps of the invention.

FIG. 5 shows in flowchart form exemplary operations of the diagnostic system 506. The diagnostic system 506 receives an input signals the MIL/CIL valve output signals. These output signals can be conveniently displayed on an oscilloscope 508 for monitoring of the valve function by a physician. The diagnostic system 506 may also be provided with data stored at 520 relating to normal operating parameters, indicative of healthy valve signal amplitude and morphology. These signals can be compared to the MIL/CIL valve signal data at 530. If there is a detectable deviation, the diagnostic system 506 will offer a series of suggested reasons for the valve malfunction. When the deviation is significant, the diagnostic system will activate an alarm 535.

The data stored in the memory device 520 may include data collected during prior examination of the particular patient or from a large selection of patients. In the preferred embodiment, the data stored will typically comprise voltage signals produced by the particular MIL/CIL valve. In addition to the MIL/CIL valve signals, other diagnostic signals (i.e. EKG-output, blood pressure, respiratory rate, temperature, etc. signals) may be jointly analyzed as indicated at 550 in order to better evaluate valve function. For example, as indicated at 540, the phase of the EKG and MIL/CIL signals may be compared.

It will be appreciated that there has been described a new method of monitoring valve conditions and operations by sensing a voltage induced in a coil by moving magnetized leaflets or by sensing the changes in voltage induced in conductors carried by leaflets moving in a magnetic field.

The above description of the invention relates to the use of the MIL and CIL valves and the method of the invention in the operating theater and post-operative, convalescent environments. The invention is also expected to be useful in long-term monitoring of valve replacement patients.

The invention has been described in an exemplary and preferred embodiment, but is not to be limited thereto. Those skilled in the art will recognize that a number of additional modifications and improvements can be made to the invention without departure from its essential spirit and scope. Therefore, the invention is not to be limited by the above disclosure, but only by the following claims.

What is claimed is:

1. Method of replacement of a heart valve of a patient with a prosthetic valve and of monitoring operation of the prosthetic valve, comprising the steps of:
   magnetizing one or more leaflets of a prosthetic valve;
   surgically replacing a dysfunctional heart valve or dysfunctional prosthetic valve with said prosthetic valve, said step of surgical replacing including the step of juxtaposing a coil of wire to the prosthetic valve; and
   monitoring the voltage induced in the coil of wire as a result of movement of the magnetized leaflets of the prosthetic valve.

2. The method of claim 1, wherein said coil is formed integrally with said valve.

3. The method of claim 2 wherein said coil is formed integrally with a base portion of said valve to which said one or more leaflets are pivotally attached.

4. The method of claim 1 wherein said valve is sutured to a vessel at its base portion.

5. The method of claim 1 wherein said leaflets are magnetized by ion implantation.

6. The method of claim 1, wherein said leaflets are magnetized by implantation of magnetized ion oxide pellets into one or more of said leaflets.

7. The method of claim 1 wherein said step of surgically replacing a dysfunctional heart valve includes the step of implanting signal conditioning and/or processing circuitry in the patient.

8. The method of claim 1 wherein said step of monitoring includes comparison of voltage signals derived from said coil with stored data.

9. The method of claim 8 wherein said stored data is data stored with respect to said patient.

10. As an article of manufacture, a prosthetic device comprising one or more magnetized leaflets, each of said one or more magnetized leaflets having at least one implanted magnetizing ion.

11. The article of claim 10 further comprising a coil of wire located in a predetermined relation to said leaflets, said coil of wire having induced therein a voltage generated by movement of said one or more magnetized leaflets.

12. The article of claim 11 wherein said coil of wire is disposed in a base portion of said valve to which said one or more magnetized leaflets are pivotally mounted.

13. The article of claim 12 wherein said base portion is adapted to be sutured to a vessel.

14. In combination:
   a prosthetic heart valve having one or more magnetized leaflets;
   a coil of wire juxtaposed to said valve in order to have a voltage induced therein as a result of movement of said magnetized leaflets; and
   a diagnostic device adapted to be connected to said coil and to analyze the voltages induced therein.

15. The combination of claim 14 wherein said coil of wire is formed integrally with said valve.

16. The combination of claim 15 wherein said coil of wire is formed within a base portion of said valve to which said leaflets are pivotally attached.

17. The combination of claim 16 wherein said base portion of said valve is adapted to be sutured to a vessel.

18. The combination of claim 14 further comprising signal processing means adapted to be implanted in the body of a patient.

19. The combination of claim 14 wherein said diagnostic device comprises means for comparing voltages induced in said coil with stored comparison data.

20. The combination of claim 19 further comprising additional physiological monitoring devices and wherein said diagnostic device comprises means for comparing voltages induced in said coil with data produced by said additional physiological monitoring devices and with stored comparison data.

21. The combination of either of claims 19 and 20 wherein said stored comparison data is derived from a particular patient for subsequent comparison.

22. The combination of claim 14, further comprising oscilloscope means for providing a visible display responsive to the voltage induced in said coil.

23. The combination of claim 14 further comprising means responsive to said diagnostic device for providing an assessment of valve condition.

24. Method of replacement of a heart valve of a patient with a prosthetic valve and of monitoring operation of the prosthetic valve, comprising the steps of:

attaching one or more conductors to one or more leaflets of a prosthetic valve;

surgically replacing a dysfunctional heart valve or dysfunctional prosthetic value with said prosthetic valve;

directing a magnetic field through the prosthetic valve; and monitoring the voltage induced in said one or more conductors as a result of movement of said one or more leaflets of the prosthetic valve.

25. The method of claim 24 wherein said magnetic field is produced by a magnetic field generated within the body of the patient.

26. The method of claim 24 wherein said magnetic field is produced by means outside the body of the patient.

27. The method of claim 24 wherein said valve comprises a base portion adapted to be sutured to a vessel.

28. The method of claim 24 wherein said conductors are formed on said leaflets by implantation thereof with conductive ions.

29. The method of claim 24 wherein said conductors are discrete wires.

30. The method of claim 24 wherein said step of surgically replacing a dysfunctional heart valve includes the step of implanting signal conditioning and processing circuitry in the patient.

31. The method of claim 24 wherein said step of monitoring includes comparison of signals derived from said one or more conductors with stored data.

32. The method of claim 31 wherein said stored data is data stored with respect to said patient.

33. As an article of manufacture, a prosthetic heart valve comprising one or more leaflets, each having one or more electrical conductors formed thereon, said one or more electrical conductors adapted for connection in a circuit loop for allowing an induced detectable voltage to be formed therein.

34. The article of claim 33 wherein said conductors are formed on said leaflets by implanted ions.

35. The article of claim 34 wherein said leaflets pivot on a base portion adapted to be sutured to a vessel.

36. In combination:

a prosthetic heart valve comprising one or more leaflets each having one or more conductors integrated therewith;

means for generating a magnetic field passing through said valve; and a diagnostic device adapted to be connected to said conductors and to analyze the voltages induced therein.

37. The combination of claim 36 wherein said magnetic field is produced by coils within the confines of the body of a patient and juxtaposed to the valve.

38. The combination of claim 36 wherein said magnetic field is produced by coils outside of the confines of the body of a patient.

39. The combination of claim 38 wherein said valve comprises a base portion adapted to be sutured to a vessel.

40. The combination of claim 36 wherein said conductors are formed by implantation of conductive ions on said leaflets.

41. The combination of claim 36 wherein said conductors are discrete wires which are integrated into said leaflets.

42. The combination of claim 36 further comprising signal processing means adapted to be implanted in the body of a patient.

43. The combination of claim 36 wherein said diagnostic device comprises means for comparing voltages induced in said conductors with stored comparison data.

44. The combination of claim 43 wherein said stored comparison data is derived from a particular patient for subsequent comparison.

45. The combination of claim 43 wherein said diagnostic device further comprises additional physiological monitoring devices and comprises means for analyzing voltages induced in said coil using signals produced by said additional devices.

46. The combination of claim 36 further comprising oscilloscope means for providing a visible display responsive to the voltage induced in said conductors.

47. The combination of claim 46 further comprising means responsive to said diagnostic device for generating an assessment of valve condition.

48. A prosthetic heart valve, comprising:

one or more magnetized leaflets adapted to move responsive to passage of blood through said valve; and a signal generation means for generating a detectable signal responsive to motion of said one or more leaflets, wherein said signal generation means is a conductor juxtaposed to said leaflets.

49. A prosthetic heart valve, comprising:

one or more magnetized leaflets adapted to move responsive to passage of blood through said valve; and a signal generation means for generating a detectable signal responsive to motion of said one or more leaflets, wherein said signal generation means is a conductor juxtaposed to said leaflets and said conductor is a coil.

50. A prosthetic heart valve, comprising:

one or more magnetized leaflets adapted to move responsive to passage of blood through said valve, and said magnetized leaflets are pivotally mounted to a generally circular based portion of said valve, adapted to be sutured to a vein; and a signal generation means for generating a detectable signal responsive to motion of said one or more leaflets, wherein said signal generation means is a conductor juxtaposed to said leaflets, said conductor is a coil and said coil is disposed around said base portion of said valve.

51. A prosthetic heart valve comprising:

one or more leaflets adapted to move responsive to passage of blood through said valve, wherein said one or more leaflets comprise conductors; and a signal generation means for generating a detectable signal responsive to motion of said one or more leaflets and said signal generation means comprises means for applying a magnetic field to said valve in operation.

52. A prosthetic heart valve comprising:

one or more leaflets adapted to move responsive to passage of blood through said valves, said one or more leaflets comprise conductors and said conductors are formed by implanted conductive ions in the surface of the one or more leaflets; and a signal generation means for generating a detectable signal responsive to motion of said one or more leaflets and said signal generation means comprises means for applying a magnetic field to said valve in operation.

53. A prosthetic heart vale, comprising:
one or more leaflets adapted to move responsive to passage of blood through said valve, said leaflets comprise conductors and said conductors comprise wires surgically integrated with said leaflets; and
a signal generation means for generating a detectable signal responsive to motion of said one or more leaflets and said signal generation means comprises means for applying a magnetic field for said valve in operation.

54. A prosthetic heart valve comprising:
one or more leaflets adapted to move responsive to passage of blood through said valve, wherein said one or more leaflets comprise conductors; and
a signal generation means for generating a detectable signal responsive to motion of said one or more leaflets, said signal generation means comprises means for applying a magnetic field to said valve in operation, and said means for applying the magnetic field is surgically implantable.

55. A prosthetic heart valve comprising:
one or more leaflets adapted to move responsive to passage of blood through said valves, said one or more leaflets comprise conductors and said conductors are formed by implanted conductive ions in the surface of the one or more leaflets; and
a signal generation means for generating a detectable signal responsive to motion of said one or more leaflets, said signal generation means comprises means for applying a magnetic field to said valve in operation, and said means for applying the magnetic field is surgically implantable.

56. A prosthetic heart valve, comprising:
one or more leaflets adapted to move responsive to passage of blood through said valve, said leaflets comprise conductors and said conductors comprise wires surgically integrated with said leaflets; and
a signal generator means for generating a detectable signal responsive to motion of said one or more leaflets, said signal generation means comprises means for applying a magnetic field for said valve in operation, and said means for applying the magnetic field is surgically implantable.

57. A prosthetic heart valve comprising one or more leaflets, each of said one or more leaflets comprising magnetic material to induce a current; and
a conductor located in predetermined relation to said leaflets, for allowing said induced current to be formed therein.

58. The article of claim 57 wherein said conductor is disposed in a base portion of said valve to which said one or more magnetized leaflets are pivotally mounted.

59. The article of claim 58 wherein said base portion is adapted to be sutured to a vessel.

60. A method of monitoring the operation of a prosthetic valve in the body, comprising the steps of:
implanting said prosthetic valve into the body, said prosthetic valve having one or more magnetized leaflets and at least one conductor for allowing a voltage to be induced therein due to relative movement with respect to the magnetized leaflets; and
monitoring the voltage induced in said at least one conductor as a result of such movement.

61. The method of claim 60, wherein said at least one conductor is formed integrally with said valve.

62. The method of claim 61, wherein said at least one conductor is formed integrally with a base portion of said valve to which said one or more leaflets are pivotally attached.

63. The method of claim 60, wherein said prosthetic valve is sutured to a vessel at its base portion.

64. The method of claim 60, wherein said leaflets are magnetized by ion implantation.

65. The method of claim 60, wherein said one or more magnetized leaflets are magnetized by implantation of magnetized iron oxide pellets.

66. The method of claim 60, wherein said step of implanting further includes the step of implanting signal conditioning and/or processing circuitry in the patient.

67. The method of claim 60, wherein the step of monitoring includes comparison of voltage signals derived from said at least one conductor with stored data.

68. The method of claim 67, wherein said stored data is data stored with respect to said patient.

69. An apparatus for monitoring the operation of a prosthetic valve in the body, comprising:
means for implanting said prosthetic valve into the body, said prosthetic valve having one or more magnetized leaflets and at least one conductor for allowing a voltage to be induced therein due to relative movement with respect to the magnetized leaflets; and
means for monitoring the voltage induced in the conductors as a result of such movement.

70. The apparatus of claim 69, wherein said at least one conductor is formed integrally with said valve.

71. The apparatus of claim 70, wherein said at least one conductor is formed integrally with a base portion of said valve, to which said one or more leaflets are pivotally attached.

72. The apparatus of claim 69, wherein said valve is sutured to a vessel at its base portion.

73. The apparatus of claim 69, wherein said leaflets are implanted with at least one magnetized ion.

74. The apparatus of claim 69, wherein said one or more magnetized leaflets are implanted with at least one magnetized iron oxide pellet.

75. The apparatus of claim 69, wherein said prosthetic valve further includes means for signal conditioning and/or processing circuitry in the patient.

76. The apparatus of claim 69, wherein said means for monitoring includes means for comparison of voltage signals derived from said at least one conductor with stored data.

77. The apparatus of claim 76, wherein said stored data is data stored with respect to said patient.

78. A prosthetic valve comprising:
one or more leaflets;
a first portion containing magnetized material;
a second portion containing at least one conductor; and
said first or second portions being carried by said leaflets causing relative movement so as to induce a voltage in said at least one conductor.

79. The apparatus of claim 78, wherein said conductor or magnetized material is formed integrally with said prosthetic valve.

80. The apparatus of claim 79, wherein said conductor or magnetized material is formed integrally with a base portion of said prosthetic valve, to which said one or more leaflets are pivotally attached.

81. The apparatus of claim 78, wherein said prosthetic valve is sutured to a vessel at its base portion.

82. The apparatus of claim 78, wherein said one or more leaflets are magnetized by implanted ions.

83. The apparatus of claim 78, wherein said one or more leaflets are magnetized by implanted magnetized iron oxide pellets.

84. The apparatus of claim 78, further comprising means for signal conditioning and/or processing circuitry in the patient.

85. The apparatus of claim 78, further comprising means for monitoring the voltage induced in said at least one conductor.

86. The apparatus of claim 85, wherein said means for monitoring further includes means for comparison with said voltage derived from said at least one conductor with stored data.

87. The method of claim 86, wherein stored data is data stored with respect to said patient.

* * * * *